United States Patent
Ra et al.

(10) Patent No.: US 9,757,506 B2
(45) Date of Patent: Sep. 12, 2017

(54) INTEGRATED KIT FOR SEPARATING BLOOD AND CONCENTRATING PRP AND METHOD FOR EXTRACTING PRP USING THE SAME

(71) Applicant: RMEDICA CO., LTD., Seoul (KR)

(72) Inventors: Jeong Chan Ra, Suwon-si (KR); Jae Wook Huh, Yongin-si (KR)

(73) Assignee: Rmedica Co., Ltd., Seoul (KR)

(*) Notice: Subject to any disclaimer, the term of this patent is extended or adjusted under 35 U.S.C. 154(b) by 159 days.

(21) Appl. No.: 14/344,990

(22) PCT Filed: Dec. 28, 2012

(86) PCT No.: PCT/KR2012/011737
§ 371 (c)(1),
(2) Date: Mar. 14, 2014

(87) PCT Pub. No.: WO2013/100700
PCT Pub. Date: Jul. 4, 2013

(65) Prior Publication Data
US 2014/0371048 A1 Dec. 18, 2014

(30) Foreign Application Priority Data
Dec. 29, 2011 (KR) .......................... 10-2011-0146247

(51) Int. Cl.
*B04B 5/04* (2006.01)
*B01L 3/14* (2006.01)
(Continued)

(52) U.S. Cl.
CPC .......... *A61M 1/3693* (2013.01); *B01L 3/5021* (2013.01); *B04B 5/04* (2013.01);
(Continued)

(58) Field of Classification Search
CPC ............. B01L 3/5021; B01L 2300/042; B01L 2300/0851; B01L 2400/0633;
(Continued)

(56) References Cited

U.S. PATENT DOCUMENTS 6,929,135 B1 * 8/2005 Hajianpour ............ B65D 47/32
215/229
9,573,130 B2 * 2/2017 Hassouneh ............. B01L 3/508
(Continued)

FOREIGN PATENT DOCUMENTS

EP 0209976 A1 * 1/1987 ............ A61M 5/315
JP 07-140136 A 6/1995
(Continued)

OTHER PUBLICATIONS

KR 20110080245 Espacenet Machine Translation.*
International Searching Authority, International Search Report of PCT/KR2012/011737 dated Apr. 25, 2013.

*Primary Examiner* — Charles Cooley
(74) *Attorney, Agent, or Firm* — Blank Rome LLP

(57) ABSTRACT

An integrated kit for separating blood and concentrating PRP includes: (a) a main body that includes an upper storage portion, a lower storage portion, and a passage portion for connecting the upper storage portion and the lower storage portion; (b) a upper cover coupled to an upper end of the upper storage portion; (c) an inner stopper inserted into a lower end of the lower storage portion so as to seal the lower storage portion; (d) a closing adjustment screw which can move vertically while penetrating a hole formed at the inner stopper and seals the passage portion; and (e) a lower cover coupled to an outside of the lower end of the lower storage portion and the outside of the inner stopper to prevent the separation of the closing adjustment screw coupled to the inner stopper in case of centrifugation.

6 Claims, 4 Drawing Sheets

(51) Int. Cl.
*A61M 1/36* (2006.01)
*B01L 3/00* (2006.01)
*G01N 33/49* (2006.01)

(52) U.S. Cl.
CPC ... *G01N 33/491* (2013.01); *A61M 2202/0415* (2013.01); *A61M 2202/0427* (2013.01); *A61M 2206/10* (2013.01); *B01L 2300/042* (2013.01); *B01L 2300/0851* (2013.01); *B01L 2400/0633* (2013.01)

(58) Field of Classification Search
CPC .............. G01N 33/491; A61M 1/3693; A61M 2206/10; B04B 5/04; B04B 5/0407; B04B 5/0414; B04B 2005/0435; B04B 2005/0485
USPC .................. 494/37, 16, 38, 40, 85; 422/533
See application file for complete search history.

(56) References Cited

U.S. PATENT DOCUMENTS

| | | | |
|---|---|---|---|
| 2003/0042161 A1* | 3/2003 | Iwamoto | A45D 40/06 206/385 |
| 2008/0213819 A1* | 9/2008 | Besson-Faure | B01L 3/5021 435/30 |
| 2014/0371048 A1* | 12/2014 | Ra | B01L 3/5021 494/37 |
| 2017/0014819 A1* | 1/2017 | U'Ren | B01L 3/50215 |

FOREIGN PATENT DOCUMENTS

| | | |
|---|---|---|
| KR | 10-2011-0009651 A | 1/2011 |
| KR | 10-2011-0046621 A | 5/2011 |
| KR | 10-2011-0080245 A | 7/2011 |
| KR | 20110080245 A * | 7/2011 |

* cited by examiner

INTEGRATED KIT FOR SEPARATING BLOOD AND CONCENTRATING PRP AND METHOD FOR EXTRACTING PRP USING THE SAME

CROSS REFERENCE TO RELATED APPLICATIONS

This application is a National Stage of International Application No. PCT/KR2012/011737 filed Dec. 28, 2012, claiming priority based on Korean Patent Application No. 10-2011-0146247, filed Dec. 29, 2011, the contents of all of which are incorporated herein by reference in their entirety.

FIELD OF THE INVENTION

The disclosure of the present invention herein relates to integrated kit for separating blood and concentrating PRP (platelet rich plasma) and a method for extracting PRP using the same, and more specifically, to integrated kit capable of separating blood and concentrating PRP in one step by using one kit and a method for extracting PRP using the same.

DESCRIPTION OF THE RELATED ART

Platelet Rich Plasma, henceforth known as PRP, refers to the blood that went through the centrifugation process after specialized treatment of the blood. This refers to the plasma that has more concentrated platelets than normal blood. It is known that platelets contain various growth factors and thus play an important role in healing scars and in skin regeneration process. It has also been reported that there are high concentrations of platelets in PRP wherein the various growth factors promote the proliferation of the surrounding cells as well as effects of stimulating the cells to synthesize the components such as collagen among others. It should be noted that PRP is being used in various areas of pain treatment such as low back pain treatment, hair loss treatment, skin regeneration and for treatment of other skin related diseases such as skin burn treatment among others.

Method for forming such PRP can be classified into chemical and physical methods. A conventional method is physical method wherein the drawn blood is centrifuged to separate blood components and the platelet poor plasma and only PRP is extracted through filter.

Conventional PRP extraction methods disclosed in Korean Patent Publication No. 2010-0105282 and 2011-0009651 are methods using two test tube, and those method comprise (1) a step wherein the blood drawn from the human body is injected into the human body and the test tube with the blood injected is centrifuged using centrifugal machine, (2) a step wherein, in a state that the separated test tube is fastened into place in order to prevent them from shaking, a injector needle is inserted to extract only plasma located on top of red blood cells, (3) a step wherein plasma that had been extracted is inserted into other test tubes and then another centrifugation process takes place in order to obtain highly concentrated PRP, and (4) a step wherein plasma located on top of the test tube that had been subjected to the second centrifugation is extracted through the injector and remaining PRP is recovered.

However, this type of test tube has problems that the red blood cells may be drawn together with the plasma in separation and extraction of the red blood cells and plasma, and the buffy coat which is rich in platelet and growth factors has a very small quantity, normally 0.1% of the blood, however, as the buffy coat is formed on top of red blood cells, the coat cannot be sufficiently extracted, and that the plasma may be exposed to air since the plasma is transferred to new test tubes after the plasma has been extracted using the injector after the first centrifugation process.

International Patent Publication No. WO2004/012750 suggested a chemical PRP extraction method wherein poly-L-glutamic acid sodium is added to the blood to selectively promotingly subject the red blood cells to agglutination and sedimentation. However, the chemical method cannot be a preferable means in that it also has a problem such as the same exposure to air as conventional physical method for separation of PRP only.

As a result of striving to solve the above-mentioned problems, the inventors found that it was possible to carry out the PRP concentration and extraction in one step by using one container without using two blood-separating containers and hemoconcentration containers, by subjecting the blood to a first centrifugation to separate a red blood cell layer and a plasma layer and adjusting a closing adjustment screw so that the red blood cell layer is placed on a lower storage portion and the plasma layer is placed on an upper storage portion and at the same time sealing a passage portion and then performing a second centrifugation, and thus the present invention has been completed.

SUMMARY OF THE INVENTION

Object of the present invention is to provide a kit capable of separating PRP layer from the blood, concentrating the PRP and extracting it in one step by using one container, without transferring the plasma layer separated after centrifugation to a separate hemoconcentration container, and a method of extracting PRP layer using the kit.

In order to achieve the above object, the present invention provides an integrated kit for separating blood and concentrating PRP layer, wherein the kit comprises (a) a main body comprising an upper storage portion, a lower storage portion, and a passage portion for connecting the upper storage portion and the lower storage portion; (b) a upper cover coupled to an upper end of the upper storage portion; (c) an inner stopper inserted into a lower end of the lower storage portion so as to seal the lower storage portion; (d) a closing adjustment screw which can move vertically while penetrating a hole formed at the inner stopper and seals the passage portion; and (e) a lower cover coupled to an outside of the lower end of the lower storage portion and the outside of the inner stopper to prevent the separation of the closing adjustment screw coupled to the inner stopper in case of centrifugation.

Furthermore, the present invention a method of extracting PRP layer by using the integrated kit for separating blood and concentrating PRP layer, wherein the method comprises (a) a step wherein collected blood is injected into the main body through the upper cover; (b) a step wherein the integrated kit for separating blood and concentrating PRP layer is placed into a centrifugal machine with the blood injected into the kit and centrifugation is then performed to separate the red blood cell layer and the plasma layer; (c) a step wherein the closing adjustment screw is moved so that the red blood cell layer is located in the lower storage portion and the plasma layer is located in the upper storage portion; (d) a step wherein the lower cover is coupled to the outside of the lower end of the lower storage portion and the outside of the inner stopper, thereby fixing the position of the closing adjustment screw; (e) a step wherein the integrated kit for separating blood and concentrating PRP layer is again placed into the centrifugal machine and centrifugation is then performed to separate the plasma layer located in the upper storage portion into the platelet rich plasma (PRP) layer and the platelet poor plasma (PPP) layer; and (f) a step wherein an injector needle is inserted to extract the PRP layer.

DETAILED DESCRIPTION OF THE EMBODIMENTS

Unless defined otherwise, all technical and scientific terms used in the specification have the same meaning as that normally understood by experts skilled in the art. In general, nomenclature used in the specification is well known in the technical field of the invention and normally used.

In one aspect, the present invention relates to an integrated kit for separating blood and concentrating PRP layer, wherein the kit comprises (a) a main body comprising an upper storage portion, a lower storage portion, and a passage portion for connecting the upper storage portion and the lower storage portion; (b) a upper cover coupled to an upper end of the upper storage portion; (c) an inner stopper inserted into a lower end of the lower storage portion so as to seal the lower storage portion; (d) a closing adjustment screw which can move vertically while penetrating a hole formed at the inner stopper and seals the passage portion; and (d) a lower cover coupled to an outside of the lower end of the lower storage portion and the outside of the inner stopper to prevent the separation of the closing adjustment screw coupled to the inner stopper in case of centrifugation.

In the following, an integrated kit for separating blood and concentrating PRP layer according to the present invention will be described in detail with reference to the attached drawings.

Figure 1:
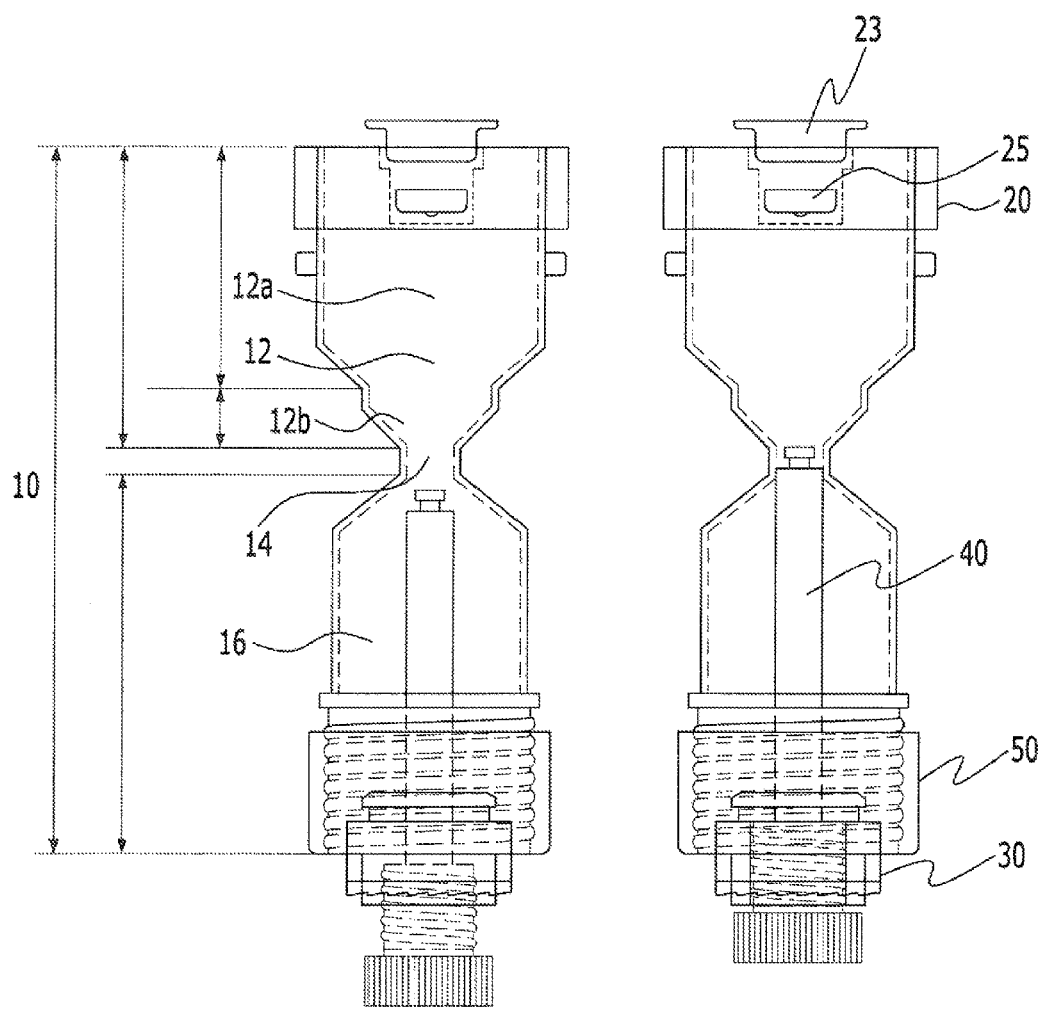
FIG. 1 is a sectional view of integrated kit for separating blood and concentrating PRP layer according to the present invention ('A' refers to the state before a passage portion is closed by a closing adjustment screw and 'B' refers to the state after the passage portion is closed by the closing adjustment screw).

FIG. 1 is a sectional view of the integrated kit for separating blood and concentrating PRP according to the present invention.

As depicted in FIG. 1, the integrated kit for separating blood and concentrating PRP layer according to the present invention comprises a main body 10 comprising an upper storage portion, a lower storage portion, and a passage portion for connecting the upper storage portion and the lower storage portion; a upper cover 20 coupled to an upper end of the upper storage portion; an inner stopper 30 inserted into a lower end of the lower storage portion so as to seal the lower storage portion; a closing adjustment screw 40 which can move vertically while penetrating a hole formed at the inner stopper and seals the passage portion; and a lower cover 50 coupled to an outside of the lower end of the lower storage portion and the outside of the inner stopper to prevent the separation of the closing adjustment screw coupled to the inner stopper in case of centrifugation.

The main body 10 separates the injected blood into a red blood cell layer and a plasma layer, and then again separates the separated plasma layer into Platelet Rich Plasma (PRP) layer and Platelet Poor Plasma (PPP) layer. The main body comprises the upper storage portion 12, the lower storage portion 16 and the passage portion 14 which connects the upper storage portion 12 and lower storage portion 16.

The upper storage portion 12 has a conical shape which becomes narrower as it goes towards lower direction and the lower storage portion 16 has a reverse conical shape which becomes narrower as it goes towards upper direction, and the passage portion 14 is formed in such a way that the lower end of the upper storage portion 12 and the upper end of the lower storage portion 16 are connected with each other in a hollow structure.

It is preferred that, in a general view, the upper storage portion 12 is in a conical structure wherein it becomes narrower towards the lower direction. However, much preferred is a structure wherein two cones are continuously coupled each of which becomes narrower as it goes towards lower direction.

Namely, The upper storage portion 12 can be divided into a first upper storage area 12a and a second upper storage area 12b, and when a second centrifugation is performed in the state of the plasma layer being placed in the upper storage portion 12 as a result of a first centrifugation, the platelet poor plasma layer is located in the first upper storage area 12a and the platelet rich plasma layer is located in the second upper storage area 12b, whereby the platelet rich plasma layer can be more easily separated.

Figure 2:
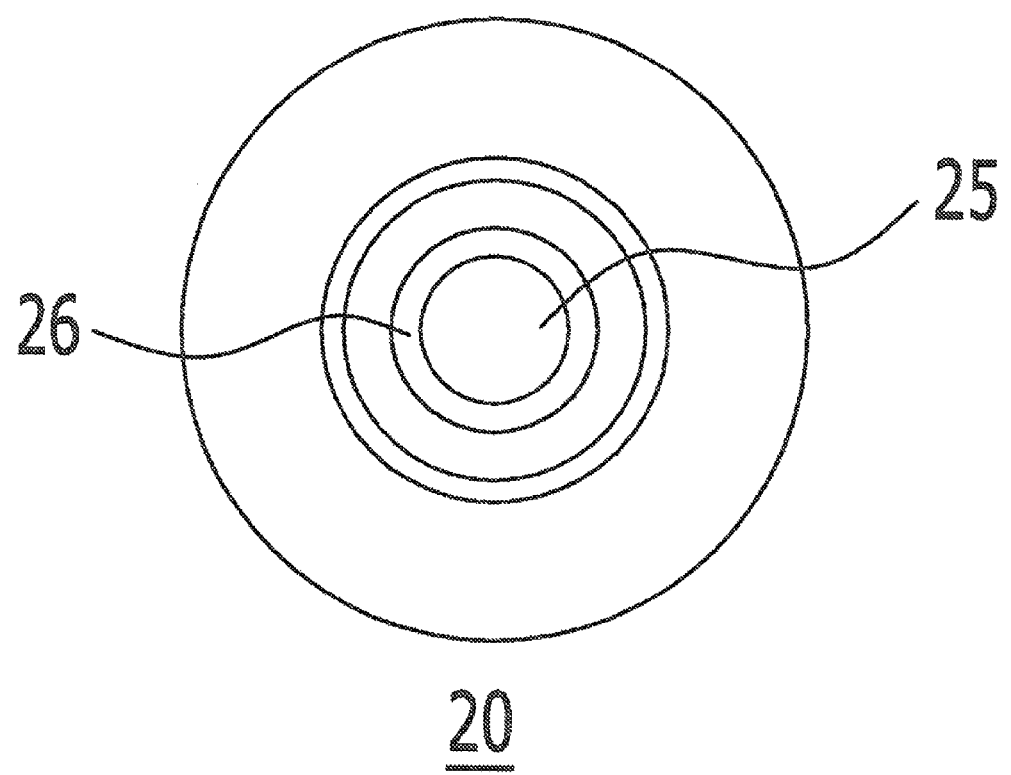
FIG. 2 is a plan view of an upper cover constituting the integrated kit for separating blood and concentrating PRP layer according to the present invention.

FIG. 2 is a plan view of the upper cover constituting the integrated kit for separating blood and concentrating PRP layer according to the present invention.

As illustrated in FIGS. 1 and 2, the upper cover 20 is coupled to the upper end of the upper storage portion 12. For the coupling, screw coupling may be used for example.

The upper cover 20 is formed with a hole located at the center of the upper cover and covered with a first silicone stopper 23 and a hole located at an inner lower part of the cover and covered with a second silicone stopper 25.

One of the characteristics is that tiny gaps 26 are formed at outer circumferential surface of the hole in order for air inside the main body to be released in injection of blood. In the state of the first and second silicone stoppers each being fitted in the holes formed inward and outward with respective to the center of the upper cover 20, the tiny gaps 26 allow air inside the main body to be release to the outside in injecting of the blood into the main body 10 through a needle, while not allowing air from the outside to seep into the main body 10.

The first silicone stopper 23 is detachable, but the second silicone stopper 25 is fixed in place.

Figure 3:
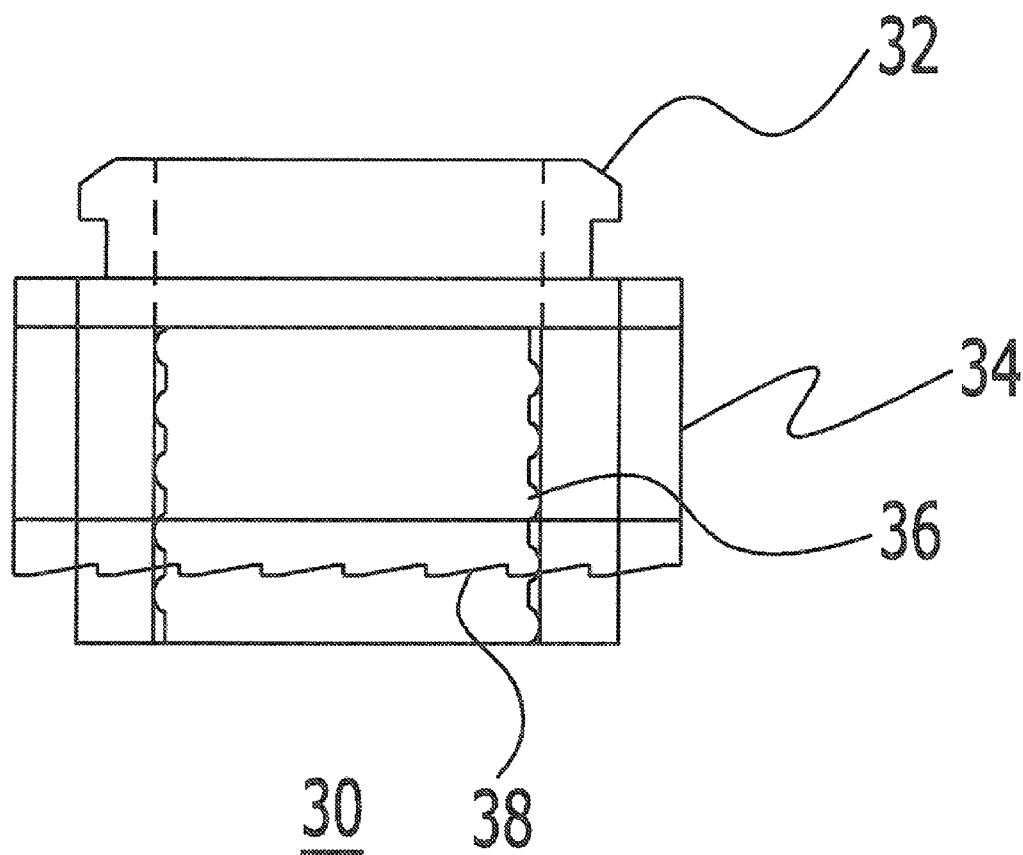
FIG. 3 is a sectional view of an inner stopper constituting the integrated kit for separating blood and concentrating PRP layer according to the present invention.

FIG. 3 is a sectional view of the inner stopper constituting the integrated kit for separating blood and concentrating PRP layer according to the present invention.

The inner stopper 30 is inserted into the lower end of the lower storage portion 16 in order to seal the lower storage portion, and comprises a silicone cover 32 and a main body 34 of the inner stopper. Namely, the silicone cover 32 is inserted to a upper end of the main body 34 of the inner stopper, and outer diameters of the silicone cover 32 and the main body 34 of the inner stopper are similar to or the same as inner diameter of the lower end of the lower storage portion 16.

The silicone cover 32 and the main body 34 of the inner stopper have a circular shape with a hole formed at the center in order for the closing adjustment screw 40 to pass through, and spiral 36 is formed within the main body 34 of the inner stopper, so that the it can be coupled to a spiral part 44 formed in the closing adjustment screw 40.

Additionally, fitting projections 38 are formed on the outside of the main body 34 of the inner stopper so as to be coupled to the lower cover 50.

The silicone cover 32 is inserted in the lower storage portion 16 and part of the main body 34 of inner stopper is located in the lower storage portion 16, and the fitting projections 38 coupled to the lower cover are located on the outside of the lower storage portion 16.

Figure 4:
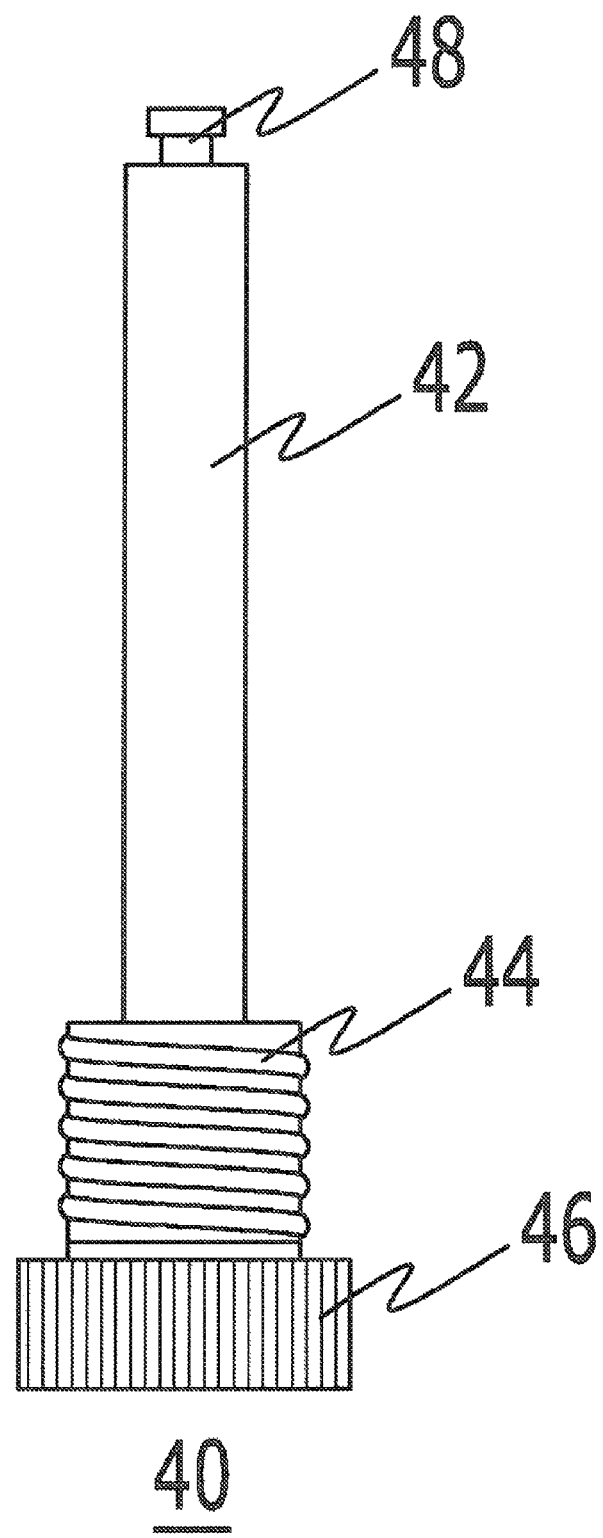
FIG. 4 is a front view of a closing adjustment screw constituting the integrated kit for separating blood and concentrating PRP according to the present invention.

FIG. 4 is a front view of the closing adjustment screw constituting the integrated kit for separating blood and concentrating PRP layer according to the present invention.

The closing adjustment screw 40 adjusts the location of the boundary between the red blood cell layer and the plasma layer after the first centrifugation process and seals the passage portion 14 in order to prevent the separated red blood cell layer and plasma layer from getting mixed up. The screw can move up and down through a hole formed in the inner stopper 30 inserted in the lower end of the lower storage portion 16.

The closing adjustment screw 40 comprises a closing rod 42, a spiral part 44 for coupling to the main body 34 of the inner stopper, and a handle part 46, and a silicone cap is joined to an end 48 of the closing rod 42. There are no restrictions in regards to the shape of silicone cap, but it is preferable for silicone cap to be in a cylindrical or conical shape in order to seal the passage portion and more easily recover the buffy coat.

Buffy coat refers to a thin lemon-yellow layer of white blood cells formed on the red blood cell layer when the blood has been centrifuged. When the blood has been centrifuged, the red blood cell layer is located on the bottommost part while the buffy coat is located right above it. The PRP layer is located above the buffy coat and the PPP layer is located on top of PRP layer.

The lower cover 50 is intended to prevent the closing adjustment screw 40 coupled to the inner stopper 30 from moving out of place during the centrifugation process, and spirals are formed on the lower cover so that it can be coupled to the outside of the lower end of the lower storage portion 16 and the fitting projections 38 of the main body of the inner stopper.

Another aspect of the present invention relates to a method of extracting PRP layer by using the integrated kit for separating blood and concentrating PRP layer wherein the method comprises (a) a step wherein collected blood is injected into the main body through the upper cover; (b) a step wherein the integrated kit for separating blood and concentrating PRP layer is placed into a centrifugal machine with the blood injected into the kit and centrifugation is then performed to separate the red blood cell layer and the plasma layer; (c) a step wherein the closing adjustment screw is moved so that the red blood cell layer is located in the lower storage portion and the plasma layer is located in the upper storage portion; (d) a step wherein the lower cover is coupled to the outside of the lower end of the lower storage portion and the outside of the inner stopper, thereby fixing the position of the closing adjustment screw; (e) a step wherein the integrated kit for separating blood and concentrating PRP layer is again placed into the centrifugal machine and centrifugation is then performed to separate the plasma layer located in the upper storage portion into the platelet rich plasma (PRP) layer and the platelet poor plasma (PPP) layer; and (f) a step wherein an injector needle is inserted to extract the PRP layer.

First, anticoagulant is placed into the injector and the blood is drawn by using the injector. It is preferred that the amount of use of anticoagulant is about 10% based on the blood to be collected. Afterwards, the collected blood is injected into the main body 10 through the upper cover 20. As previously explained, since the hole located at the center of the upper cover is covered with the first silicone stopper 23 and the hole located at the inner lower part of the cover is covered with the second silicone stopper 25, the injector needle passes through the first silicone stopper 23 and the second silicone stopper 25 to inject the blood.

Since the tiny gaps 26 are formed in the upper cover 20, in the state of the silicone stoppers 23, 25 each being fitted in the holes formed outward and inward with respective to the center of the upper cover 20, air from the outside is not almost allowed to seep into the main body 10, but air inside the main body can be release to the outside in injecting of the blood into the main body 10 through the needle. Therefore, unlike a conventional blood-separating container, it is not necessary to open an exposing hole for letting the inside air out in injection of the blood, whereby the secondary airborne infection can be minimized.

For the next step, the integrated kit for separating blood and concentrating PRP layer is placed into the centrifugal machine with the blood injected into the kit and the centrifugation is then performed to separate the red blood cell layer and the plasma layer.

When the integrated kit for separating blood and concentrating PRP layer has been firstly centrifuged, the red blood cell layer is located in the lower storage portion and the plasma layer is located on the red blood cell layer.

Thus, the closing adjustment screw 40 is moved upward or downward so that the red blood cell layer is located in the lower storage portion and the plasma layer is located in the upper storage portion, thereby adjusting the position of the boundary between the red blood cell layer and the plasma layer to a lower part of the passage portion 14 or to an upper part of lower storage portion 16, and at the same time the passage portion 14 is closed by the silicone cap coupled to the end 48 of the closing rod 42 of the closing adjustment screw 40.

A second centrifugation must be performed in order to further separate the plasma layer located in the passage portion 14 and the upper storage portion 12 into the PRP layer and the PPP layer. In this connection, the lower cover 50 is coupled to the outside of the lower end of lower storage portion 16 and the fitting projections 38 of the main body 34 of the inner stopper as outside thereof in order to prevent the position of the closing adjustment screw 40 from being moving backward in centrifugation.

After the lower cover 50 has been coupled to the outside of the lower end of lower storage portion 16 and the fitting projections 38 of the main body 34 of the inner stopper, the integrated kit for separating blood and concentrating PRP layer is again placed into the centrifugal machine and centrifugation is then performed to separate the plasma layer located in the upper storage portion into the platelet rich plasma (PRP) layer and the platelet poor plasma (PPP) layer.

Lastly, the first silicone stopper 23 of the upper cover 20 is removed, and PPP layer and the remaining PRP layer are extracted by passing the injector needle through the second silicone stopper 25.

In the following, the present invention will be described in more detail through an example. This example is only for the purpose of illustrating the present invention. It is obvious to a person skilled in the relevant art that the scope of the present invention is not limited by the example.

Example 1: Extraction of the PRP Layer from the Blood 18 cc of the blood is drawn to the injector containing 2 cc of the anticoagulant, and the blood is then injected into the main body by passing the injector needle through the first and second silicone stoppers of the integrated kit for separating blood and concentrating PRP layer.

Next, the integrated kit for separating blood and concentrating PRP layer is placed in the centrifugal machine to be centrifuged for three minutes at 3000 rpm.

After taking the integrated kit for separating blood and concentrating PRP layer out of the centrifugal machine, the closing adjustment screw is moved upward or downward to adjust the position of the boundary between the red blood cell layer and plasma layer towards the upper part of the lower storage portion, and the passage portion is closed by coming into close contact with the silicone cap coupled to the end of the closing rod of the closing adjustment screw. Then, the lower cover is turned to be coupled to the outside of the lower end of the lower storage portion and fitting projections of the main body of the inner stopper, thereafter, the integrated kit for separating blood and concentrating PRP layer is again placed in the centrifugal machine to be centrifuged for four minutes at 3000 rpm.

The integrated kit for separating blood and concentrating PRP layer is removed after the centrifugation process, and thereafter, the first silicone stopper of the upper cover is removed and the injector needle is inserted through the second silicone stopper to extract the PPP layer and again extract 4 cc of the remaining PRP layer.

DESCRIPTION OF REFERENCE NUMERALS

10: Main body
12: Upper storage portion
14: Passage portion
16: Lower storage portion
20: Upper cover
23: First silicon stopper
25: Second silicon stopper
26: Gap
30: Inner stopper
32: Silicone cover
34: Main body of the inner stopper
38: Fitting projection
40: Closing adjustment screw
42: Closing rod
44: Spiral part
46: Handle part
50: Lower cover

INDUSTRIAL APPLICABILITY

By using the integrated kit for separating blood and concentrating PRP layer according to the present invention, it is possible to extract PRP from the blood in one step without moving a plasma layer separated after centrifugation to a separate hemoconcentration container, and thus secondary airborne infection can be minimized.

As above, specific parts of the present invention have been described in detail. It is obvious to a person skilled in the art that such particular techniques are only preferred embodiments and the scope of the present invention is not limited by the embodiments. Therefore, the substantial scope of the present invention is defined by the appended claims and equivalents thereof.

What is claimed is:

1. An integrated kit for separating blood and concentrating PRP layer, wherein the kit comprises:
   (a) a main body comprising an upper storage portion, a lower storage portion, and a passage portion for connecting the upper storage portion and the lower storage portion;
   (b) an upper cover coupled to an upper end of the upper storage portion;
   (c) an inner stopper including a main body inserted into a lower end of the lower storage portion so as to seal the lower storage portion, wherein fitting projections are formed on the outside of the main body of the inner stopper;
   (d) a closing adjustment screw which can move vertically while penetrating a hold formed at the inner stopper as the closing adjustment screw rotates along a spiral groove and seals the passage portion, and
   (e) a lower cover coupled to an outside of the lower end of the lower storage portion, to the fitting projection formed on the outside of the main body and the outside of the inner stopper to prevent the separation of the closing adjustment screw coupled to the inner stopper in case of centrifugation.

2. The integrated kit for separating blood and concentrating PRP layer of claim 1, wherein the upper storage portion has a conical shape which becomes narrower as it goes towards lower direction and the lower storage portion has a reverse conical shape which become narrower as it goes towards upper direction, and the passage portion is a part where the lower end of the upper storage portion and the upper end of the lower storage portion are connected with each other in a hollow structure.

3. The integrated kit for separating blood and concentrating PRP layer of claim 1, wherein the upper cover is formed with a hole located at the center of the upper cover and covered with a first silicone stopper and a hole located at an inner lower part of the cover and covered with a second silicone stopper.

4. The integrated kit for separating blood and concentrating PRP layer of claim 3, wherein tiny gaps are formed at outer circumferential surface of the holes covered with the first and second silicone stoppers in order for air inside the main body to be released in injection of blood.

5. The integrated kit for separating blood and concentrating PRP layer of claim 1, wherein the inner stopper is covered with a silicone cap in order to seal the lower storage portion, and is coupled to the closing adjustment screw through a spiral formed within the inner stopper.

6. A method of extracting PRP layer by using the integrated kit for separating blood and concentrating PRP layer of claim 1, wherein the method comprises:
   (a) a step wherein collected blood is injected into the main body through the upper cover;
   (b) a step wherein the integrated kit for separating blood and concentrating PRP layer is placed into a centrifugal machine with the blood injected into the kit and centrifugation is then performed to separate the red blood cell layer and the plasma layer;
(c) a step wherein the closing adjustments screw is moved so that the red blood cell layer is located in the lower storage portion and the plasma layer is located in the upper storage portion;
(d) a step wherein the lower cover is coupled to the outside of the lower end of the lower storage portion, the outside of the inner stopper and the fitting projections, thereby fixing the position of the closing adjustment screw;
(e) a step wherein the integrated kit for separating blood and concentrating PRP layer is again placed in to the centrifugal machine and centrifugation is then performed to separate the plasma layer located in the upper storage portion into the platelet rich plasma (PRP) layer and the platelet poor plasma (PPP) layer; and
(f) a step wherein an injector needle is inserted to extract the PRP layer.

* * * * *